United States Patent
Atagi et al.

(10) Patent No.: US 8,502,984 B2
(45) Date of Patent: Aug. 6, 2013

(54) OPTICAL MEASUREMENT APPARATUS

(75) Inventors: Hidehiro Atagi, Hirakata (JP); Shuichi Yamada, Hirakata (JP); Masanori Nakano, Yawata (JP); Eiji Kawata, Tokyo (JP); Shuichi Akashi, Tokyo (JP); Hiroyuki Kuroki, Tokyo (JP)

(73) Assignees: Otsuka Electronics Co., Ltd., Hirakata-Shi (JP); Toppan Printing Co., Ltd., Tokyo (JP)

( * ) Notice: Subject to any disclaimer, the term of this patent is extended or adjusted under 35 U.S.C. 154(b) by 209 days.

(21) Appl. No.: 13/188,448

(22) Filed: Jul. 21, 2011

(65) Prior Publication Data

US 2012/0019831 A1 Jan. 26, 2012

(30) Foreign Application Priority Data

Jul. 21, 2010 (JP) ................................. 2010-163990

(51) Int. Cl.
*G01N 21/55* (2006.01)

(52) U.S. Cl.
USPC ........................................................ 356/445

(58) Field of Classification Search
None
See application file for complete search history.

(56) References Cited

U.S. PATENT DOCUMENTS

| | | | | |
|---|---|---|---|---|
| 3,390,274 A | * | 6/1968 | Hunt | 250/227.3 |
| 3,480,786 A | * | 11/1969 | Kottman | 250/559.48 |
| 4,271,022 A | * | 6/1981 | Dixon et al. | 210/198.2 |
| 4,894,551 A | * | 1/1990 | Kishimoto et al. | 250/559.23 |
| 5,287,423 A | * | 2/1994 | Anthony | 385/26 |
| 7,339,169 B1 | * | 3/2008 | Eckels et al. | 250/339.07 |
| 7,346,245 B2 | * | 3/2008 | Terakawa et al. | 385/116 |
| 7,872,749 B2 | * | 1/2011 | Robertson et al. | 356/326 |
| 2001/0017054 A1 | * | 8/2001 | Narita et al. | 73/105 |
| 2010/0032583 A1 | * | 2/2010 | Kane | 250/458.1 |

FOREIGN PATENT DOCUMENTS

| | | |
|---|---|---|
| JP | 07-294704 | 11/1995 |
| JP | 10-058131 | 3/1998 |
| JP | 2000-158174 | 6/2000 |

* cited by examiner

*Primary Examiner* — Gordon Stock, Jr.
(74) *Attorney, Agent, or Firm* — Ditthavong Mori & Steiner, P.C.

(57) ABSTRACT

An optical measurement apparatus using an optical fiber to measure the characteristic of an object to be measured arranged along the circumference of a circle includes a first pulley, a second pulley which is turnable on its own axis at a second angular velocity while revolving about the first pulley at a first angular velocity, and the optical fiber which is held by the second pulley and projects detection light on the object to be measured and receives reflected light from the object to be measured. The first angular velocity and the second angular velocity are the same in magnitude and opposite in the direction. Occurrence of a twist in the optical fiber is suppressed, and therefore, the optical measurement apparatus is capable of measuring the characteristics of the object to be measured with high accuracy.

4 Claims, 10 Drawing Sheets

OPTICAL MEASUREMENT APPARATUS

BACKGROUND OF THE INVENTION

1. Field of the Invention

The present invention relates to an optical measurement apparatus that uses an optical fiber to project detection light on an object to be measured and to receive reflected light from the object to be measured, thereby to measure the characteristic of the object to be measured.

2. Description of the Background Art

In an optical measurement apparatus, an optical fiber directs detection light oscillated at an oscillator to an object to be measured. The optical fiber projects (irradiates) the detection light toward the object to be measured. The detection light is reflected by the object to be measured. The optical fiber receives the reflected light and directs it to a detector. The detector measures the spectrum, absorbance or the like of the reflected light. Based on the spectrum, absorbance or the like of the reflected light, the optical measurement apparatus can measure (analyze) the characteristic (concentration or chemical species, for example) of the object to be measured.

The object to be measured is arranged in various manners according to a desired purpose. A common optical measurement apparatus measures the characteristic of an object to be measured with the object to be measured being arranged at a predetermined position in a fixed manner, because moving an object to be measured relative to a fixed optical fiber is highly likely to lead to a decrease in measurement accuracy. Therefore, in a common optical measurement apparatus, an optical fiber is moved relative to an object to be measured arranged in a fixed manner, in a two-dimensional direction or in a three-dimensional direction.

Japanese Patent Laying-Open No. 2000-158174 discloses a laser beam machining apparatus which performs three-dimensional machining using an optical fiber cable which transmits laser light. Japanese Patent Laying-Open No. 10-058131 discloses a light beam heating device which has a condensing lens mechanism attached on a tip of an optical fiber and turned around the optical axis. Japanese Patent Laying-Open No. 07-294704 discloses an apparatus for forming an antireflection film for an optical fiber connector. The apparatus forms an antireflection film on an optical fiber.

SUMMARY OF THE INVENTION

An object of the present invention is to provide an optical measurement apparatus capable of measuring the characteristic of an object to be measured with higher accuracy by suppressing occurrence of a twist in an optical fiber in using the optical fiber to measure the characteristic of the object to be measured arranged along the circumference of a circle.

An optical measurement apparatus according to a first aspect of the present invention is an optical measurement apparatus which uses an optical fiber to measure the characteristic of an object to be measured arranged along the circumference of a circle. The optical measurement apparatus includes a fixed body, a rotating body and the optical fiber.

The rotating body is turnable on its own axis at a second angular velocity while revolving about the fixed body at a first angular velocity. The optical fiber is held by the rotating body and projects detection light on the object to be measured and receives reflected light from the object to be measured. The first angular velocity and the second angular velocity are the same in magnitude and opposite in direction.

An optical measurement apparatus according to a second aspect of the present invention is the optical measurement apparatus according to the first aspect wherein the fixed body has a first circular portion having a circular external shape, the rotating body has a second circular portion having a circular external shape, and the first circular portion and the second circular portion have the same diameter. This optical measurement apparatus further includes an annular belt member surrounding an outer circumferential surface of the first circular portion and an outer circumferential surface of the second circular portion.

An optical measurement apparatus according to a third aspect of the present invention is the optical measurement apparatus according to the first aspect wherein the fixed body has a first toothed wheel portion formed like a toothed wheel, the rotating body has a second toothed wheel portion formed like a toothed wheel and having the same diameter as a diameter of the first toothed wheel portion. This optical measurement apparatus further includes a toothed wheel arranged between the first toothed wheel portion and the second toothed wheel portion.

An optical measurement apparatus according to a fourth aspect of the present invention is the optical measurement apparatus according to the first aspect wherein a revolution direction of the rotating body is configured to be reversed every time the rotating body revolves about the fixed body by a predetermined angle.

The present invention can provide an optical measurement apparatus capable of measuring the characteristic of an object to be measured with higher accuracy by suppressing occurrence of a twist in an optical fiber in using the optical fiber to measure the characteristic of the object to be measured arranged along the circumference of a circle.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An optical measurement apparatus in each embodiment based on the present invention will be hereinafter described with reference to the drawings. When any reference to a number, an amount and the like is made in the description below, the scope of the present invention is not necessarily limited to that number, amount and the like unless otherwise specified. In the description below, the same or corresponding parts have the same reference numbers allotted, and description thereof may not be repeated. It is originally intended to combine and use configurations of embodiments shown below as appropriate, unless otherwise limited.

First Embodiment

Configuration of Optical Measurement Apparatus 1A

Referring to FIGS. 1 to 5, the configuration of an optical measurement apparatus 1A in the present embodiment will be described.

Figure 1:
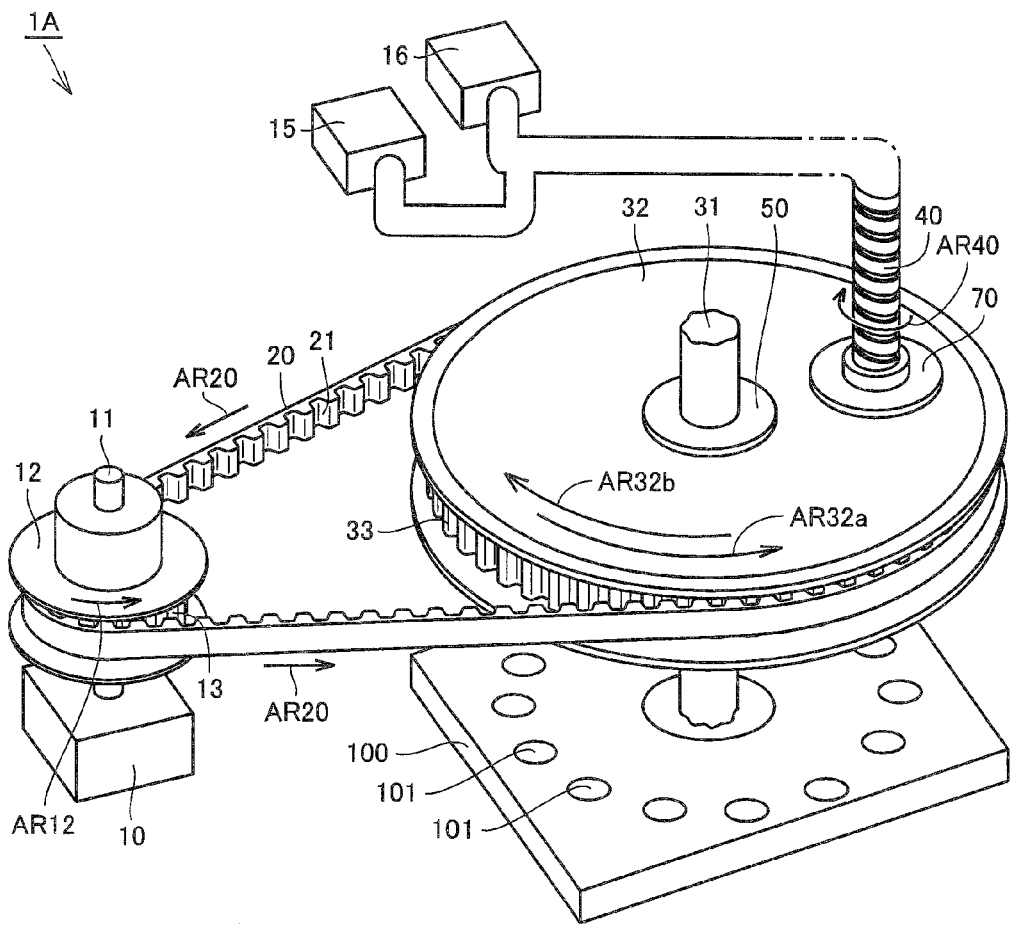
FIG. 1 is a first perspective view illustrating an optical measurement apparatus in a first embodiment (and another configuration of the first embodiment).
Figure 2:
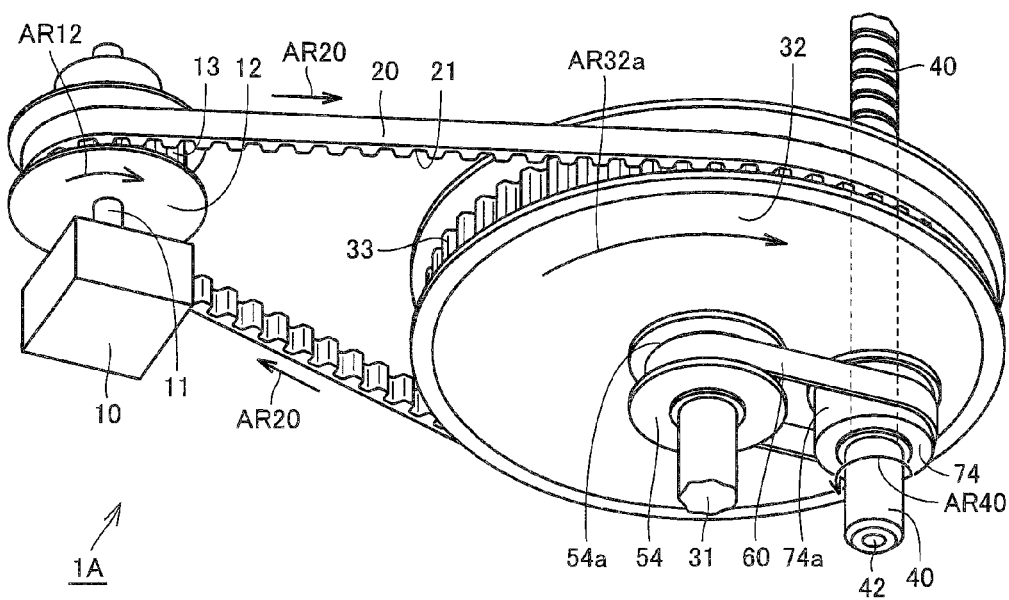
FIG. 2 is a second perspective view illustrating the optical measurement apparatus in the first embodiment.

Referring to FIGS. 1 and 2, optical measurement apparatus 1A includes a rotary driver 10, toothed wheels 12, 32, a toothed belt member 20, a support shaft 31 (rotation shaft), an optical fiber 40, a belt member 60 (see FIG. 2), a pulley 54 (fixed body), a pulley 74 (rotating body), an oscillator 15, and a detector 16.

Toothed wheel 12 is supported by a rotation shaft 11. Toothed wheel 12 receives rotational power through rotation shaft 11 from rotary driver 10. Toothed wheel 12 is rotatable with rotation shaft 11 in the direction of an arrow AR12 and in the direction opposite thereto.

Toothed belt member 20 is annularly configured and has an inner circumferential surface 21 on which concavities and convexities are formed. The concavities and convexities correspond to the shape of an outer circumferential surface 13 of toothed wheel 12, which is formed like a toothed wheel, as well as to the shape of an outer circumferential surface 33 of toothed wheel 32, which is formed like a toothed wheel. Toothed belt member 20 is placed on outer circumferential surfaces 13, 33 in a manner to surround outer circumferential surfaces 13, 33. Toothed belt member 20 receives power from toothed wheel 12 and is rotatable in the direction of arrow AR20 and in the direction opposite thereto.

Figure 3:
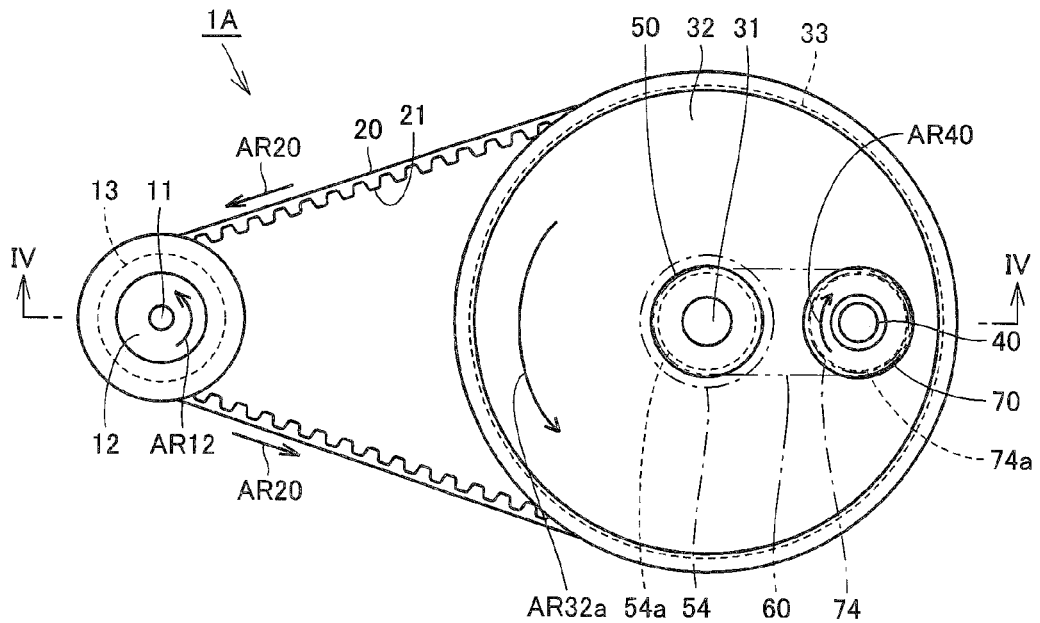
FIG. 3 is a plan view illustrating the optical measurement apparatus in the first embodiment.
Figure 4:
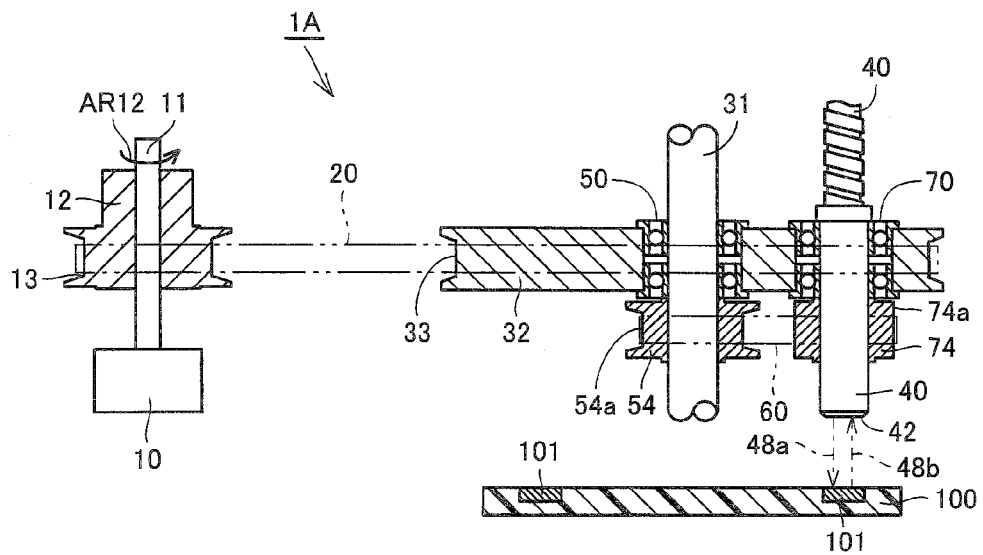
FIG. 4 is a cross sectional view taken along a line IV-IV and seen in the direction of arrows in FIG. 3.

Referring to FIGS. 3 and 4, support shaft 31 is supported by a predetermined frame (not shown) in a fixed manner. Pulley 54 is attached and fixed to support shaft 31 at a longitudinally (in the vertical direction when seen in FIG. 4) predetermined height position thereof. Pulley 54 has a circular portion 54a (first circular portion) having a circular external shape. Toothed wheel 32 is arranged above pulley 54 and coaxially with pulley 54.

Between toothed wheel 32 and support shaft 31, a bearing 50 is provided. Toothed wheel 32 is supported by bearing 50 rotatably around support shaft 31. Toothed wheel 32 receives power from toothed belt member 20 and is rotatable in the direction of an arrow AR32a and in the direction opposite thereto (in the direction of AR32b in FIG. 1). When toothed wheel 32 rotates, support shaft 31 and pulley 54 do not rotate.

Optical fiber 40 has one end (above when seen in FIG. 4) connected to oscillator 15 (see FIG. 1) and detector 16 (see FIG. 1). Optical fiber 40 has the other end side (below when seen in FIG. 4) extending through a part of toothed wheel 32 at a position which is spaced apart from support shaft 31. Between toothed wheel 32 and optical fiber 40, a bearing 70 is provided.

Optical fiber 40 is supported by bearing 70 rotatably relative to toothed wheel 32. Bearing 70 enables optical fiber 40 to rotate (turn on its own axis) relative to toothed wheel 32 in the direction of an arrow AR40 (see FIG. 1) and in the direction opposite thereto.

Pulley 74 is attached to optical fiber 40, coaxially with optical fiber 40 and on a tip side of optical fiber 40 located below the lower surface of toothed wheel 32. Pulley 74 and optical fiber 40 are rotatable (turnable on their own axes) in an integrated manner. Furthermore, pulley 74 and optical fiber 40 are rotatable (revolvable) around support shaft 31 in an integrated manner through the rotation of toothed wheel 32 around support shaft 31.

As shown in FIG. 4, pulley 74 is located at approximately the same height as pulley 54. Pulley 74 has a circular portion 74a (second circular portion) having a circular external shape. Circular portion 54a of pulley 54 and circular portion 74a of pulley 74 are configured to have the same diameter. Belt member 60 is placed on the outer circumferential surface of circular portion 54a and the outer circumferential surface of circular portion 74a in a manner to surround them.

Figure 5:
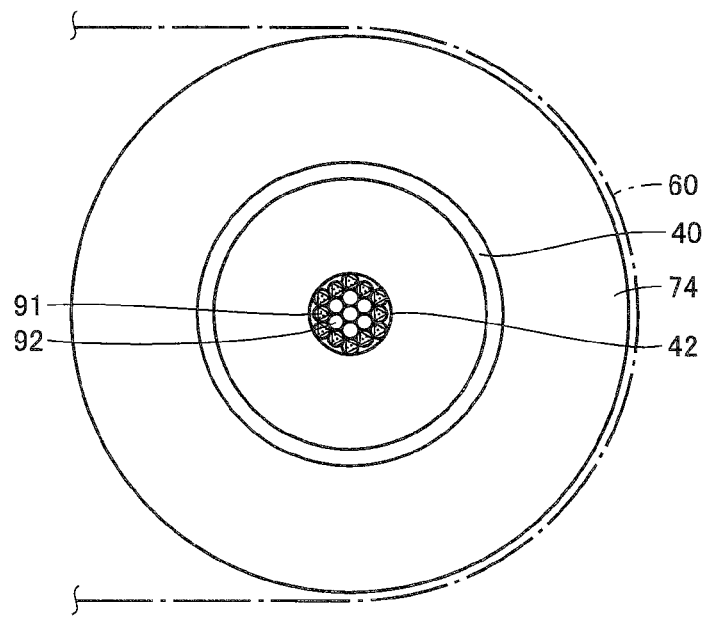
FIG. 5 is a bottom view illustrating a tip portion of an optical fiber of the optical measurement apparatus in the first embodiment.

Referring to FIG. 5, optical fiber 40 has a tip portion 42 where a plurality of light projecting fibers 91 and light receiving fibers 92 are provided in an exposed manner. Optical fiber 40 in optical measurement apparatus 1A has twelve light projecting fibers 91 arrayed in a regular hexagonal shape and seven light receiving fibers 92 arranged to fill inside the regular hexagonal array. In optical measurement apparatus 1A, light projecting fibers 91 and light receiving fibers 92 are arranged symmetrically about a point.

Referring to FIGS. 1 and 4, for optical measurement apparatus 1A configured as above, a sample unit 100 is arranged below toothed wheel 32. Sample unit 100 has a surface on which a plurality of objects to be measured 101 are arranged along the circumference of a circle. Each object to be measured 101 is arranged opposite to (tip portion 42 of) optical fiber 40, which rotates (revolves).

Operation of Optical Measurement Apparatus 1A

Referring to FIGS. 6 to 9, operation of optical measurement apparatus 1A will be described.

Figure 6:
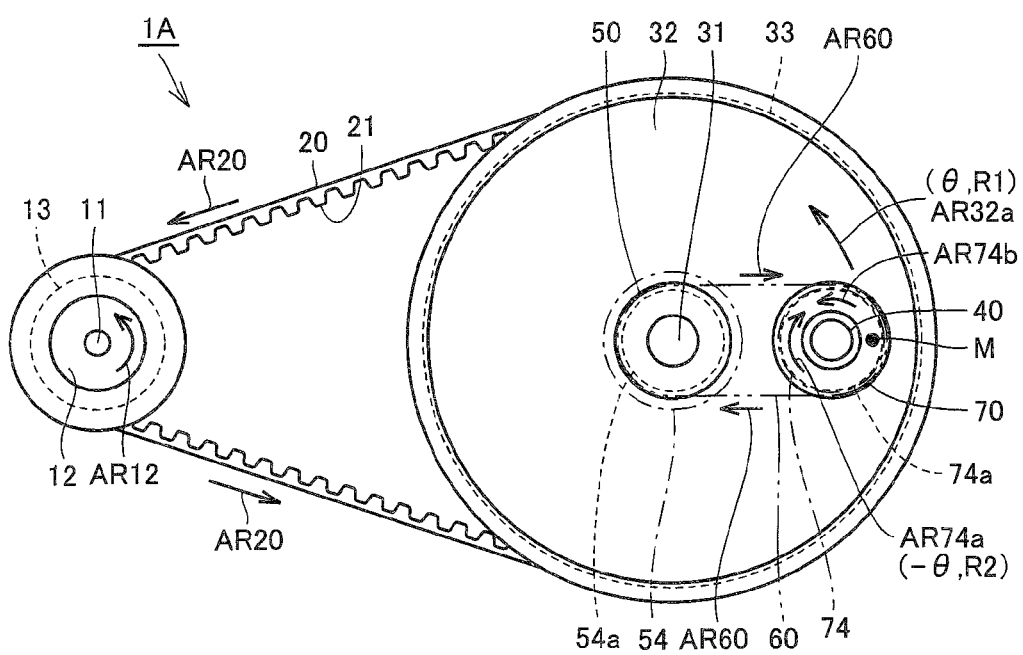
FIG. 6 is a plan view illustrating a first rotating state of the optical measurement apparatus in the first embodiment.

Referring to FIG. 6, in a first rotating state, toothed wheel 12 rotates in the direction of arrow AR12. Toothed belt member 20 rotates in the direction of arrow AR20. Toothed wheel 32 rotates in the direction of arrow AR32a. Now, suppose that toothed wheel 32 rotates by an angle θ (for example, 90°) in the direction of arrow AR32a in a time period T.

With the rotation of toothed wheel 32, pulley 74 revolves about pulley 54 by angle θ. Pulley 74 revolves at a first angular velocity R1 (=angle θ/time T) in the direction of arrow AR32a. At this time, although toothed wheel 32 rotates, pulley 54 does not rotate.

With the revolution of pulley 74 in the direction of arrow AR32a, pulley 74 tries to rotate (turn on its own axis) in the direction of an arrow AR74b (the direction opposite to the direction of an arrow AR74a). In other words, pulley 74 tries to have a change in the absolute phase angle in a rotational direction.

Belt member 60 is placed on pulley 54 arranged in a fixed manner. Whereas pulley 74 tries to have a change in the absolute phase angle in a rotational direction, belt member 60 acts to force (the outer circumferential surface of) pulley 74 to rotate in the direction of an arrow AR60. Consequently, with revolution of pulley 74 in the direction of arrow AR32a, pulley 74 rotates (turns on its own axis) in the direction of arrow AR74a at a second angular velocity R2. First angular velocity R1 and second angular velocity R2 are opposite in direction.

In optical measurement apparatus 1A, circular portion 54a and circular portion 74a are configured to have the same diameter, and therefore, first angular velocity R1 and second angular velocity R2 are the same in magnitude (velocity distribution). When toothed wheel 32 rotates by angle θ in the direction of arrow AR32a in time period T, pulley 74 rotates relative to toothed wheel 32 by angle (−θ) in the direction of arrow AR74a in time period T. Belt member 60 acts on pulley 74 in a manner to offset a change in the absolute phase angle in a rotational direction of pulley 74.

Figure 7:
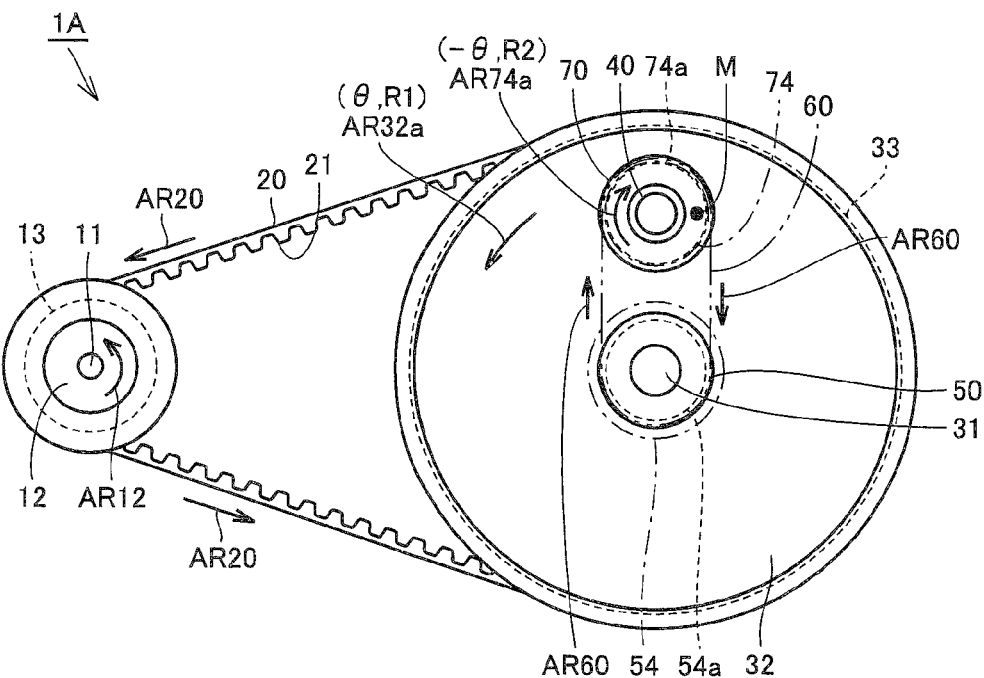
FIG. 7 is a plan view illustrating a second rotating state of the optical measurement apparatus in the first embodiment.

As shown in a second rotating state in FIG. 7, the position of a reference position M (marked for the convenience of description) has not changed from that in the first rotating state in FIG. 6. In other words, the absolute phase angle in a rotational direction of reference position M did not change before and after the rotation of toothed wheel 32 by angle θ and is always located rightmost when seen in the drawing.

Even with rotation of toothed wheel 32, pulley 74 does not have any change in the absolute phase angle, and therefore, optical fiber 40 will not rotate (turn on its own axis). Optical measurement apparatus 1A suppresses occurrence of a twist in optical fiber 40.

In the second rotating state in FIG. 7, suppose that toothed wheel 32 rotates further by an angle θ (90°). Optical fiber 40 revolves further around support shaft 31 by angle θ in the direction shown by arrow AR32a.

Figure 8:
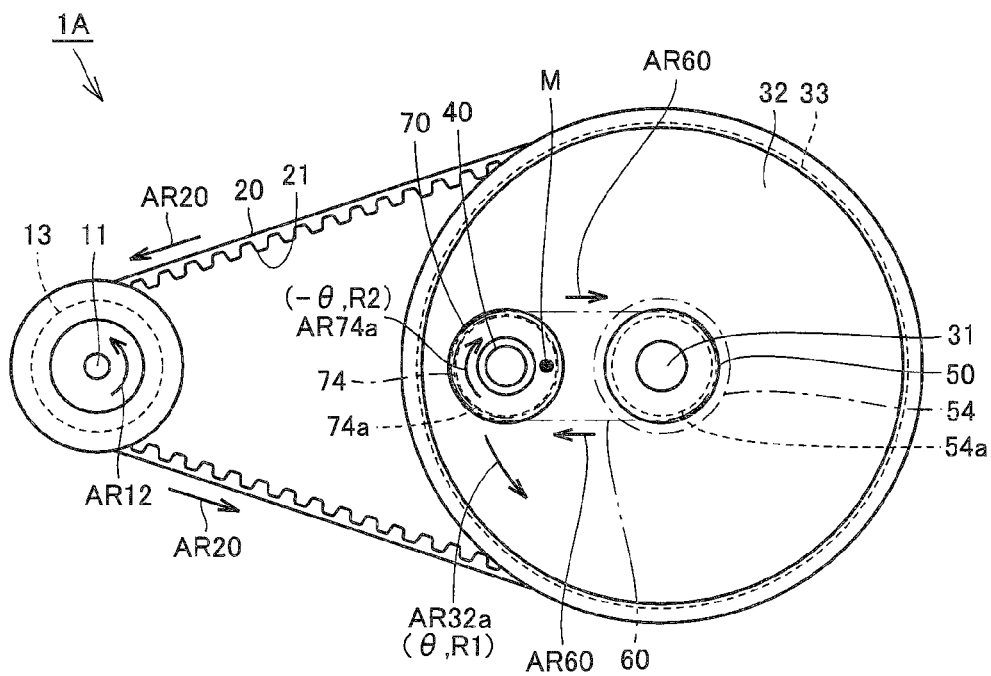
FIG. 8 is a plan view illustrating a third rotating state of the optical measurement apparatus in the first embodiment.

As shown in a third rotating state in FIG. 8, the position of reference position M has not changed from that in the second rotating state in FIG. 7. The absolute phase angle in a rotational direction of reference position M is always located rightmost when seen in the drawings. No twist occurred in optical fiber 40 before and after the rotation of toothed wheel 32 by angle θ.

Likewise, in the third rotating state in FIG. 8, suppose that toothed wheel 32 rotates further by angle θ (90°). Optical fiber 40 revolves further around support shaft 31 by angle θ in the direction shown by arrow AR32a.

Figure 9:
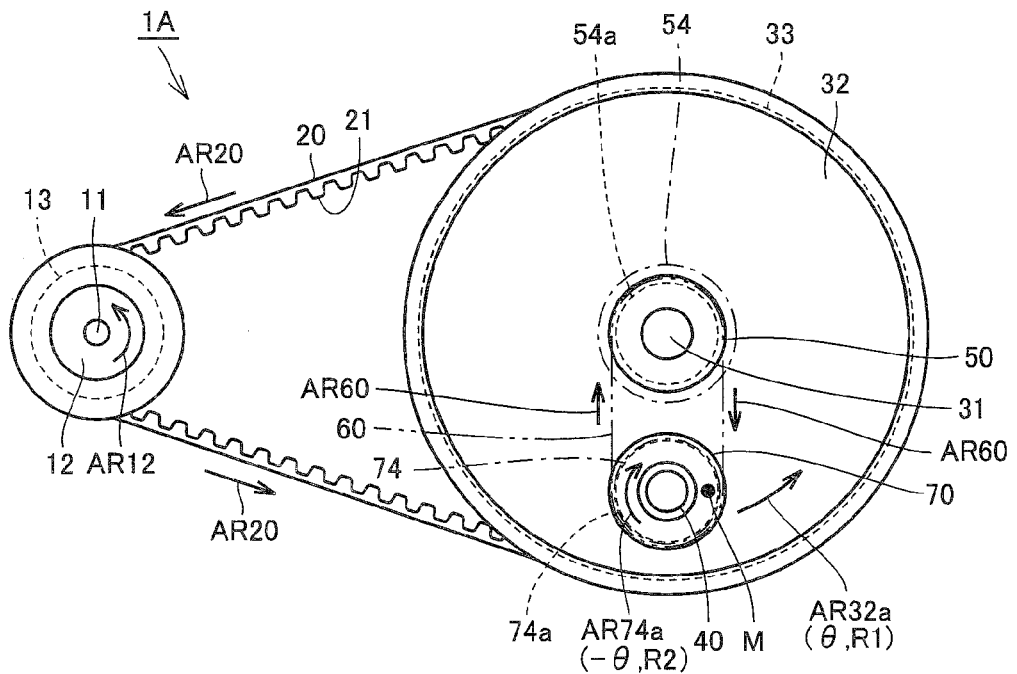
FIG. 9 is a plan view illustrating a fourth rotating state of the optical measurement apparatus in the first embodiment.

As shown in a fourth rotating state in FIG. 9, the position of reference position M has not changed from that in the third rotating state in FIG. 8. The absolute phase angle in a rotational direction of reference position M is always located rightmost when seen in the drawing. No twist occurred in optical fiber 40 before and after the rotation of toothed wheel 32 by angle θ.

Optical measurement apparatus 1A does not cause any twist to occur in optical fiber 40 even if optical fiber 40 revolves around support shaft 31a plurality of times.

Since no twist occurs in optical fiber 40, detection light 48a (see FIG. 4) directed within light projecting fiber 91 and reflected light 48b directed within light receiving fiber 92 are prevented from being affected by such a twist. Detection light 48a which is generated at oscillator 15 and based on desired setting conditions is directed by light projecting fiber 91 and projected on object to be measured 101 (see FIG. 4) with the setting conditions being maintained. Reflected light 48b from object to be measured 101 is received by light receiving fiber 92 and directed to detector 16 (see FIG. 1) with a spectrum or the like (light balance), which indicates the characteristic of object to be measured 101, being maintained.

In using optical fiber 40 to measure the characteristic of an object to be measured arranged along the circumference of a circle, optical measurement apparatus 1A does not cause any twist to occur in optical fiber 40, and therefore, does not cause any change in the characteristics (spectrum or the like) of detection light 48a and reflected light 48b. Optical measurement apparatus 1A enables measuring the characteristic of an object to be measured (photometric data) with higher accuracy. Optical measurement apparatus 1A does not cause any twist to occur in optical fiber 40, and therefore, also enables achieving a longer life of optical fiber 40.

It should be noted that in optical measurement apparatus 1A, toothed wheel 12 and toothed wheel 32 may be configured like a pulley, and toothed belt member 20 may be configured like a rubber belt which has no concavity or convexity. Pulley 54 and pulley 74 may be configured like a toothed wheel and belt member 60 may be configured like a toothed belt.

Another Configuration of First Embodiment

In the above-described first embodiment, the description was given based on a mode in which optical fiber 40 (pulley 74) receives rotational power from rotary driver 10 and revolves around support shaft 31 (pulley 54) in the direction of arrow AR32a a plurality of times.

Referring to FIG. 1, optical fiber 40 (pulley 74) may be configured to reverse its rotational direction every time it makes one revolution about support shaft 31 (pulley 54). In other words, optical fiber 40 makes one revolution in the direction of arrow AR32a, then reverses its rotational direction and makes one revolution in the direction of arrow AR32b. Optical fiber 40 may be configured to repeat these rotational and reverse motions a plurality of times.

As for the case where optical fiber 40 is configured to repeat the above-described rotational and reverse motions a plurality of times, the rotational angle of optical fiber 40 is not limited to 360°. Optical fiber 40 rotates, for example, by 180° in the direction of arrow AR32a, then reverses its rotational direction and rotates again by 180° in the direction of arrow AR32b. Optical fiber 40 may be configured to repeat such rotational and reverse motions a plurality of times.

The rotational angle is also not limited to 180° and may be 120° or may be 90°. Any angle can be employed as the rotational angle. It is preferable that the rotational angle be determined to correspond to the positions where a plurality of objects to be measured 101 are arranged respectively on the surface of sample unit 100. In addition, the rotational angle above may be determined such that only some objects to be measured 101 of a plurality of objects to be measured 101 are measured. For example, if ten objects to be measured 101 are carried on sample unit 100 and arrayed on the circumference of a circle, the rotational angle above may be determined such that measurement is performed only on adjacent three of the ten objects to be measured, or the rotational angle above may be determined such that measurement is performed intermittently on only three objects to be measured that are spaced apart from each other.

The number of times the rotational and reverse motions are performed may be configured such that a rotational motion (360°, 180°, 120° or the like) is performed once (in one direction) for one sample unit 100, the one sample unit 100 is replaced with another sample unit 100, and subsequently, a reverse motion (−360°, −180°, −120° or the like) is performed once (in the direction opposite to the one direction above) for the other sample unit 100. The number of times the rotational and reverse motions are performed for one sample unit 100 should be determined depending on a method of measurement.

Still Another Configuration of First Embodiment

In the above-described first embodiment, the description was given based on a mode in which light projecting fibers 91 and light receiving fibers 92 of optical fiber 40 are arrayed symmetrically about a point. Light projecting fibers 91 and light receiving fibers 92 may be arrayed asymmetrically about a point.

Figure 10:
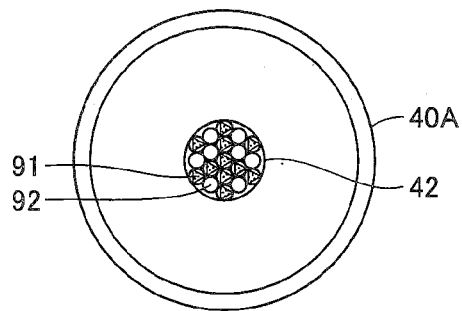
FIG. 10 is a bottom view illustrating a first example of an optical fiber in a still another configuration of the first embodiment.

For example, as in optical fiber 40A shown in FIG. 10, eleven light projecting fibers 91 and eight light receiving fibers 92 may be arrayed symmetrically about a line. In optical fiber 40A, six light projecting fibers 91 are arrayed on the respective vertices of a regular hexagonal shape, three light projecting fibers 91 are arrayed in a linear array inside the regular hexagonal shape, and two light projecting fibers 91 are respectively arrayed on both sides of the linear array. Six receiving fibers 92 are arrayed on the respective sides of the regular hexagonal shape, arrayed inside which are two light projecting fibers 91.

In a case where light projecting fibers 91 and light receiving fibers 92 are arrayed symmetrically about a line as in optical fiber 40A, since optical fiber 40A does not rotate (no twist occurs), it is possible to measure the characteristic of an object to be measured (photometric data) with higher accuracy. The same applies to optical fibers 40B to 40D, which will be described below. It should be noted that even in a case where light projecting fibers 91 and light receiving fibers 92 are arrayed asymmetrically, since optical fiber 40A does not rotate (no twist occurs), it is possible to measure the characteristic of an object to be measured (photometric data) with higher accuracy.

Figure 11:
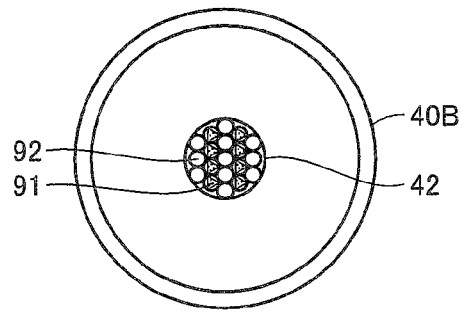
FIG. 11 is a bottom view illustrating a second example of the optical fiber in the still another configuration of the first embodiment.

As in optical fiber 40B shown in FIG. 11, eight light projecting fibers 91 and eleven light receiving fibers 92 may be arrayed symmetrically about a line. In optical fiber 40B, three light receiving fibers 92 are arrayed linearly, which is adjacent to four light projecting fibers 91 arrayed linearly, which is adjacent to five light receiving fibers 92 arrayed linearly. Furthermore, light projecting fibers 91 and light receiving fibers 92 are configured to be laterally symmetrical with respect to those five light receiving fibers 92.

Figure 12:
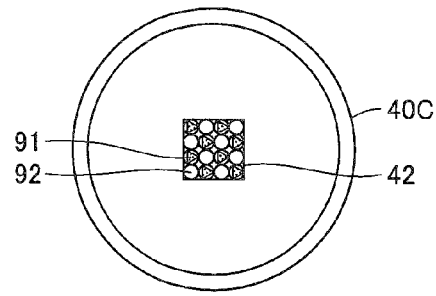
FIG. 12 is a bottom view illustrating a third example of the optical fiber in the still another configuration of the first embodiment.

As in an optical fiber 40C shown in FIG. 12, eight light projecting fibers 91 and eight light receiving fibers 92 may be arrayed symmetrically about a line. In optical fiber 40C, light projecting fibers 91 and light receiving fibers 92 are arrayed in a staggered manner within a rectangular shape.

Figure 13:
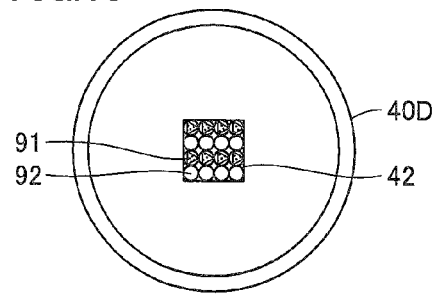
FIG. 13 is a bottom view illustrating a fourth example of the optical fiber in the still another configuration of the first embodiment.

As in optical fiber 40D shown in FIG. 13, eight light projecting fibers 91 and eight light receiving fibers 92 may be arrayed symmetrically about a line. In optical fiber 40D, a linear array of four light projecting fibers 91 and a linear array of four light receiving fibers 92 are arrayed in an alternating manner within a rectangular shape.

Even in a case where light projecting fibers 91 and light receiving fibers 92 are arrayed symmetrically about a line as in optical fibers 40A to 40D, since an optical fiber does not rotate (no twist occurs), it is possible to measure the characteristic of an object to be measured (photometric data) with higher accuracy. Even in a case where light projecting fibers 91 and light receiving fibers 92 are arranged asymmetrically, an optical fiber which does not rotate (no twist occurs) enables measuring the characteristic of an object to be measured (photometric data) with higher accuracy.

Second Embodiment

Configuration of Optical Measurement Apparatus 1B

Figure 14:
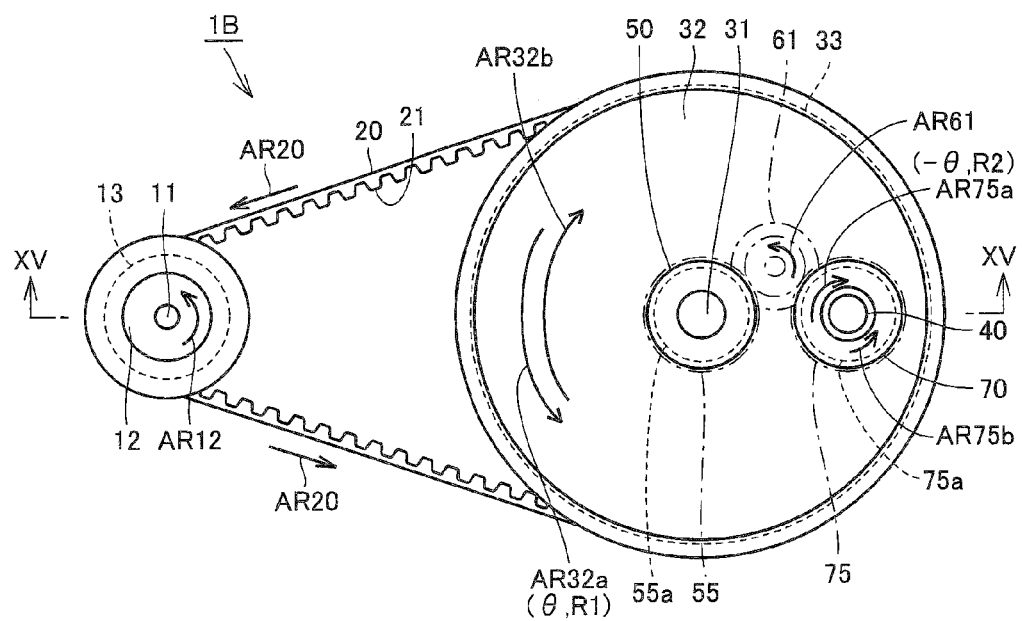
FIG. 14 is a plan view illustrating an optical measurement apparatus in a second embodiment.
Figure 15:
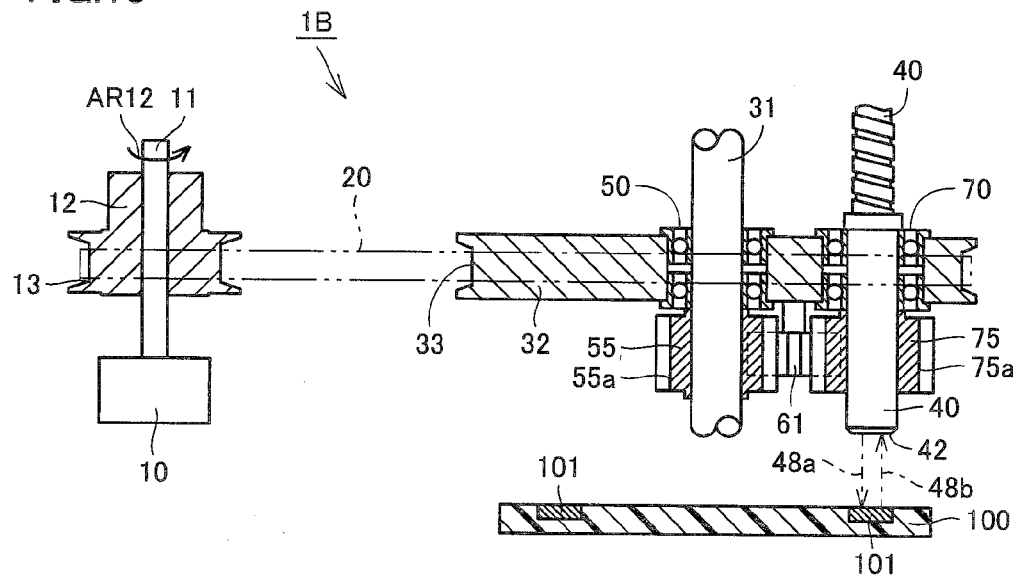
FIG. 15 is a cross sectional view taken along a line XV-XV and seen in the direction of arrows in FIG. 14.

Referring to FIGS. 14 and 15, an optical measurement apparatus 1B in the present embodiment will be described. Here, description will be given on the difference from optical measurement apparatus 1A in the above-described first embodiment.

Optical measurement apparatus 1B includes a toothed wheel 55 (fixed body), a toothed wheel 75 (rotating body) and a toothed wheel 61, instead of pulley 54, pulley 74, and belt member 60 in optical measurement apparatus 1A of the above-described first embodiment.

Toothed wheel 55 is attached and fixed to support shaft 31 at a longitudinally (in the vertical direction when seen in FIG. 15) predetermined height position thereof. Toothed wheel 55 has a toothed wheel portion 55a (first toothed wheel portion) formed like a toothed wheel. Toothed wheel 32 is arranged above toothed wheel 55 and coaxially with toothed wheel 55. When toothed wheel 32 rotates, toothed wheel 55 does not rotate.

Toothed wheel 75 is attached to optical fiber 40, coaxially with optical fiber 40 and on the tip side of optical fiber 40 located below the lower surface of toothed wheel 32. Toothed wheel 75 and optical fiber 40 are rotatable (turnable on their own axes) in an integrated manner. Furthermore, toothed wheel 75 and optical fiber 40 are rotatable (revolvable) around support shaft 31 in an integrated manner through the rotation of toothed wheel 32 around support shaft 31.

Toothed wheel 75 is located at approximately the same height as toothed wheel 55. Toothed wheel 75 has a toothed wheel portion 75a (second toothed wheel portion) having a toothed-wheel-like external shape. Toothed wheel portion 55a of toothed wheel 55 and toothed wheel portion 75a of toothed wheel 75 are configured to have the same diameter.

Toothed wheel 61 corresponds to the shapes of the outer circumferential surface of toothed wheel portion 55a and the outer circumferential surface of toothed wheel portion 75a and is rotatably held by and between toothed wheel portion 55a and toothed wheel portion 75a.

Operation of Optical Measurement Apparatus 1B

Referring to FIG. 14, toothed wheel 12 rotates in the direction of arrow AR12. Toothed belt member 20 rotates in the direction of arrow AR20. Toothed wheel 32 rotates in the direction of arrow AR32a.

With the rotation of toothed wheel 32, toothed wheel 75 revolves about toothed wheel 55 by angle θ (first angular velocity R1) in the direction of arrow AR32a. At this time, although toothed wheel 32 rotates, toothed wheel 55 does not rotate.

With the revolution of toothed wheel 75 in the direction of arrow AR32a, toothed wheel 75 tries to rotate (turn on its own axis) in the direction of an arrow AR75b. In other words, toothed wheel 75 tries to have a change in the absolute phase angle in a rotational direction.

Toothed wheel 61 is rotatably held by and between toothed wheel 55 and toothed wheel 75. Whereas toothed wheel 75 tries to have a change in the absolute phase angle in a rotational direction, toothed wheel 61 revolves in the direction of arrow AR32a while turning on its own axis in the direction of an arrow AR61. Toothed wheel 61 acts, on its contact surface with toothed wheel 75, to force toothed wheel 75 to rotate in the direction of an arrow AR75a. Consequently, with revolution of toothed wheel 75 in the direction of arrow AR32a, toothed wheel 75 rotates (turns on its own axis) in the direction of arrow AR75a at second angular velocity R2. First angular velocity R1 and second angular velocity R2 are in the opposite direction.

In optical measurement apparatus 1B, toothed wheel portion 55a and toothed wheel portion 75a are configured to have the same diameter, and therefore, first angular velocity R1 and second angular velocity R2 are the same in magnitude (velocity distribution). When toothed wheel 32 rotates by angle θ in the direction of arrow AR32a in time period T, toothed wheel 75 rotates relative to toothed wheel 32 by angle (−θ) in the direction of arrow AR75a in time period T. Toothed wheel 61 acts on toothed wheel 75 in a manner to offset a change in the absolute phase angle in a rotational direction of toothed wheel 75.

Even with rotation of toothed wheel 32, toothed wheel 75 does not have any change in the absolute phase angle, and therefore, optical fiber 40 will not rotate (turn on its own axis). Optical measurement apparatus 1B also suppresses occurrence of a twist in optical fiber 40. Consequently, the same effect as that in optical measurement apparatus 1A in the above-described first embodiment can be obtained.

As with the other configuration of the above-described first embodiment, optical fiber 40 may be configured to make one revolution in the direction of arrow AR32a, then reverse its rotational direction, make one revolution in the direction of arrow AR32b, and repeat these motions. As with the still another configuration of the above-described first embodiment, optical fiber 40 may have light projecting fibers 91 and light receiving fibers 92 arrayed symmetrically about a line.

Another Configuration of Second Embodiment

Figure 16:
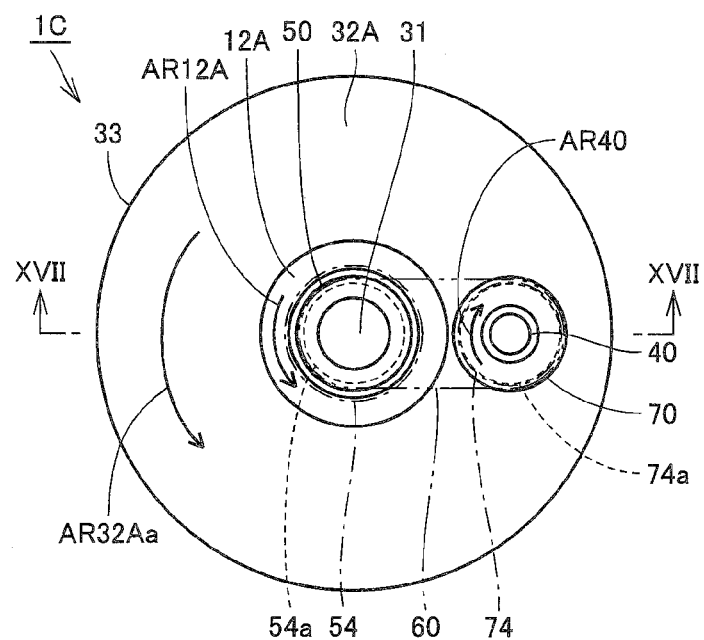
FIG. 16 is a plan view illustrating an optical measurement apparatus in another configuration of the second embodiment.
Figure 17:
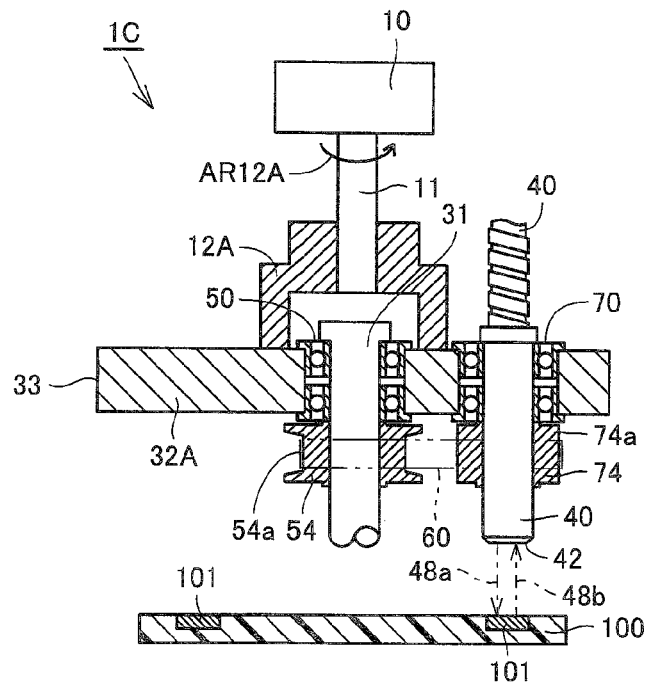
FIG. 17 is a cross sectional view taken along a line XVII-XVII and seen in the direction of arrows in FIG. 16.

Referring to FIGS. 16 and 17, an optical measurement apparatus 1C in another configuration of the second embodiment will be described. Here, description will be given on the difference from optical measurement apparatus 1A in the above-described first embodiment.

Optical measurement apparatus 1C includes a coupling member 12A and a disk member 32A instead of toothed wheel 12, toothed wheel 32 and belt member 20 in optical measurement apparatus 1A of the above-described first embodiment. Disk member 32A is configured to be approximately the same as toothed wheel 32. Disk member 32A has an outer circumferential surface 33 which does not need to be configured like a toothed wheel. It should be noted that, for convenience of illustration, rotary driver 10 and rotation shaft 11 are illustrated only in FIG. 17 and that FIG. 16 schematically shows (only a lower end portion side of) coupling member 12A.

In optical measurement apparatus 1C, rotary driver 10 is arranged above disk member 32A (see FIG. 17). Rotation shaft 11 suspended from rotary driver 10 is arranged coaxially with support shaft 31. Rotation shaft 11 has a lower portion to which coupling member 12A is attached. Coupling member 12A receives rotational power through rotation shaft 11 from rotary driver 10. Coupling member 12A is rotatable with rotation shaft 11 in the direction of arrow AR12A and in the direction opposite thereto.

The lower end of coupling member 12A is configured annularly and coupled to an upper surface of disk member 32A. Disk member 32A receives power from coupling member 12A and is rotatable in the direction of an arrow AR32Aa and in the direction opposite thereto.

As with optical measurement apparatus 1C, even with a configuration in which power from rotary driver 10 is directly transmitted to disk member 32A which supports optical fiber 40 (a configuration in which power is transmitted without being routed through belt member 60 or the like), the same effect as that in optical measurement apparatus 1A in the above-described first embodiment can be obtained. Even if optical fiber 40 revolves around support shaft 31a plurality of times, no twist occurs in optical fiber 40. Further, optical measurement apparatus 1C also enables achieving space-saving in a planer direction.

Still Another Configuration of Second Embodiment

Figure 18:
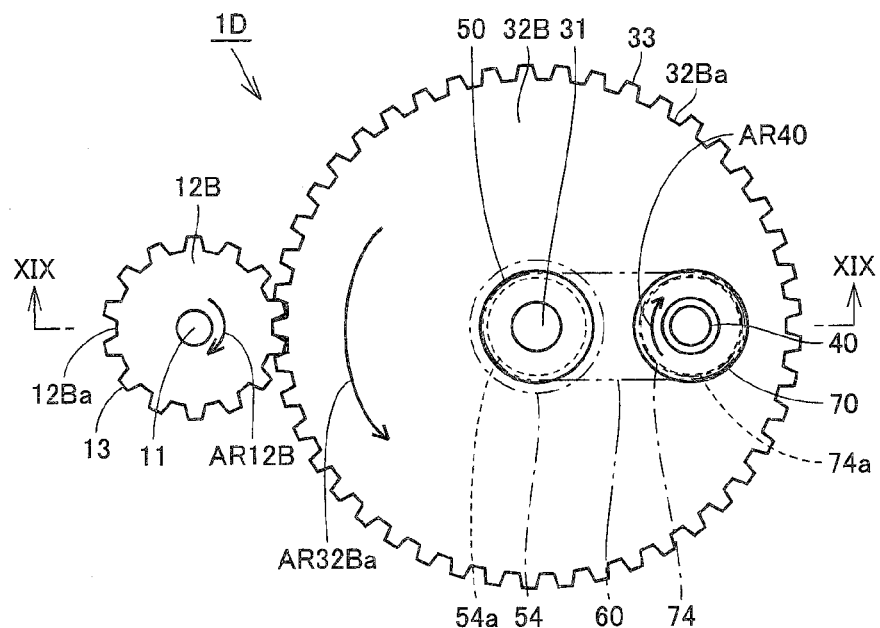
FIG. 18 is a plan view illustrating an optical measurement apparatus in still another configuration of the second embodiment.
Figure 19:
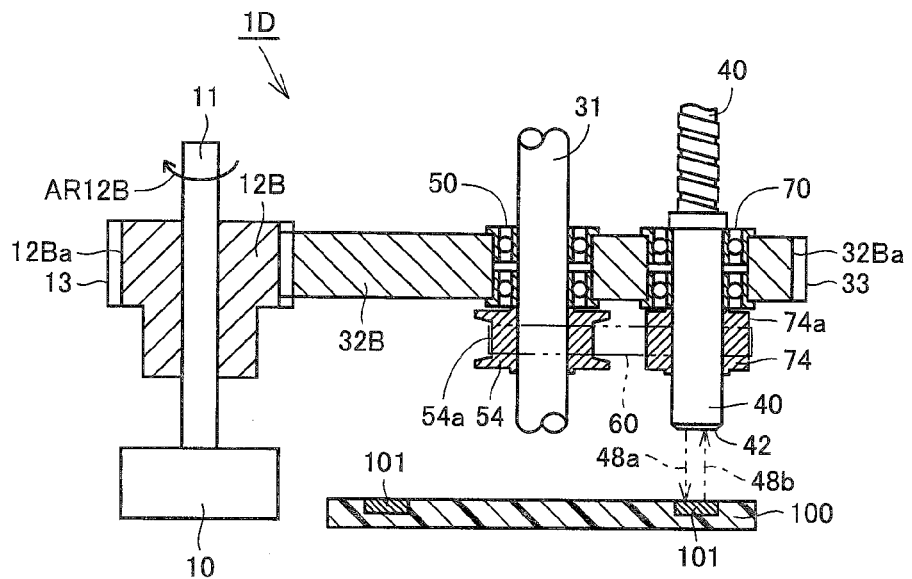
FIG. 19 is a cross sectional view taken along a line XIX-XIX and seen in the direction of arrows in FIG. 18.

Referring to FIGS. 18 and 19, an optical measurement apparatus 1D in still another configuration of the second embodiment will be described. Here, description will be given on the difference from optical measurement apparatus 1A in the above-described first embodiment.

Optical measurement apparatus 1D includes a toothed wheel 12B and a toothed wheel 32B instead of toothed wheel 12, toothed wheel 32 and belt member 20 in optical measurement apparatus 1A of the above-described first embodiment. A toothed wheel portion 12Ba formed on outer circumferential surface 13 of toothed wheel 12B corresponds to a toothed wheel portion 32Ba formed on outer circumferential surface 33 of toothed wheel 32B. Toothed wheel 12B and toothed wheel 32B are arranged such that toothed wheel portion 12Ba and toothed wheel portion 32Ba engage with each other.

Toothed wheel 12B receives rotational power through rotation shaft 11 from rotary driver 10. Toothed wheel 12B is rotatable with rotation shaft 11 in the direction of an arrow AR12B and in the direction opposite thereto. Toothed wheel 32B receives power from toothed wheel 12B and is rotatable in the direction of an arrow AR32Ba and in the direction opposite thereto.

As with optical measurement apparatus 1A in the above-described first embodiment, optical measurement apparatus 1D does not cause any twist to occur in optical fiber 40 even if optical fiber 40 revolves around support shaft 31a plurality of times. Optical measurement apparatus 1D also enables achieving space-saving in a planer direction.

Third Embodiment

Figure 20:
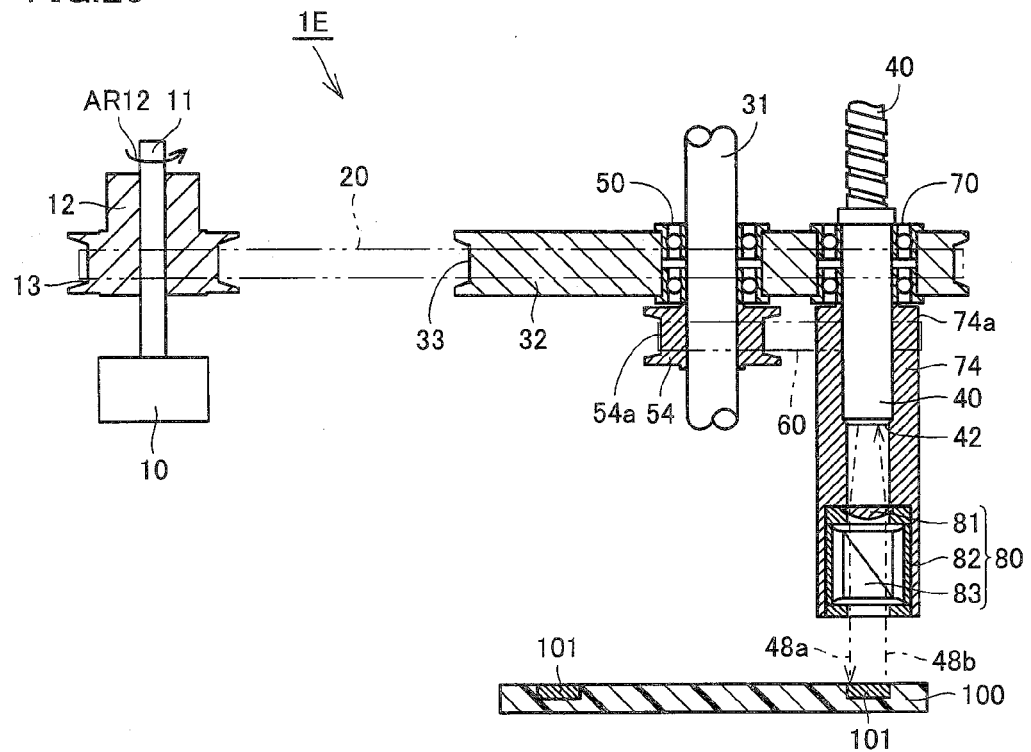
FIG. 20 is a cross sectional view illustrating an optical measurement apparatus in a third embodiment.

Referring to FIG. 20, an optical measurement apparatus 1E in the present embodiment will be described. Here, description will be given on the difference from optical measurement apparatus 1A in the above-described first embodiment.

In optical measurement apparatus 1E, pulley 74 extends toward tip portion 42 of optical fiber 40 (in a manner to approach sample unit 100). Pulley 74 is formed to be hollow inside, and pulley 74 has a lower end side provided with a polarizing element 80. Polarizing element 80 is composed of a lens part 81, a housing 82 and a polarizing filter 83 (polarizing prism).

Detection light 48a projected from light projecting fiber 91 of optical fiber 40 passes through lens part 81 and is polarized in polarizing filter 83 at a particular wave length. Detection light 48a is projected on object to be measured 101 in a polarized state. Reflected light 48b from object to be measured 101 passes through polarizing element 80 again and directed by light receiving fiber 92 to detector 16 (see FIG. 1).

Providing polarizing element 80 integrally with pulley 74 as in optical measurement apparatus 1E results in that no twists occurs in optical fiber 40 and, additionally, that the relative positional relationship in a rotational direction between optical fiber 40 and polarizing element 80 does not change. Optical measurement apparatus 1E enables measuring the characteristic of an object to be measured (photometric data) with higher accuracy even in a case where polarizing element 80 is used.

Another Configuration of Third Embodiment

Figure 21:
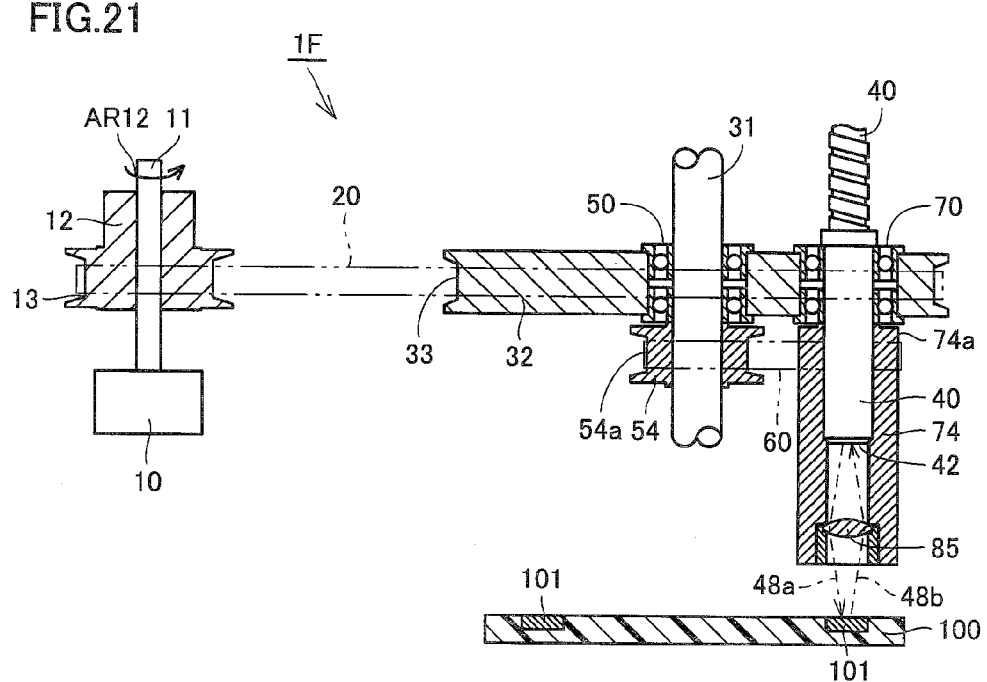
FIG. 21 is a cross sectional view illustrating an optical measurement apparatus in another configuration of the third embodiment.

Referring to FIG. 21, an optical measurement apparatus 1F in another configuration of the third embodiment will be described. Here, description will be given on the difference from optical measurement apparatus 1A in the above-described first embodiment.

In optical measurement apparatus 1F, pulley 74 extends toward tip portion 42 of optical fiber 40 (in a manner to approach sample unit 100). Pulley 74 is formed to be hollow inside, and pulley 74 has a lower end side provided with a condensing lens 85.

Detection light 48a projected from light projecting fiber 91 of optical fiber 40 passes through condensing lens 85 and projected on object to be measured 101 in a condensed state. Reflected light 48b from object to be measured 101 passes through condensing lens 85 again and directed by light receiving fiber 92 to detector 16 (see FIG. 1).

Providing condensing lens 85 integrally with pulley 74 as in optical measurement apparatus 1F results in that no twist occurs in optical fiber 40 and, additionally, that the relative positional relationship in a rotational direction between optical fiber 40 and condensing lens 85 does not change. Optical measurement apparatus 1F enables measuring the characteristic of an object to be measured (photometric data) with higher accuracy even in a case where condensing lens 85 is used.

Still Another Configuration of Third Embodiment

Figure 22:
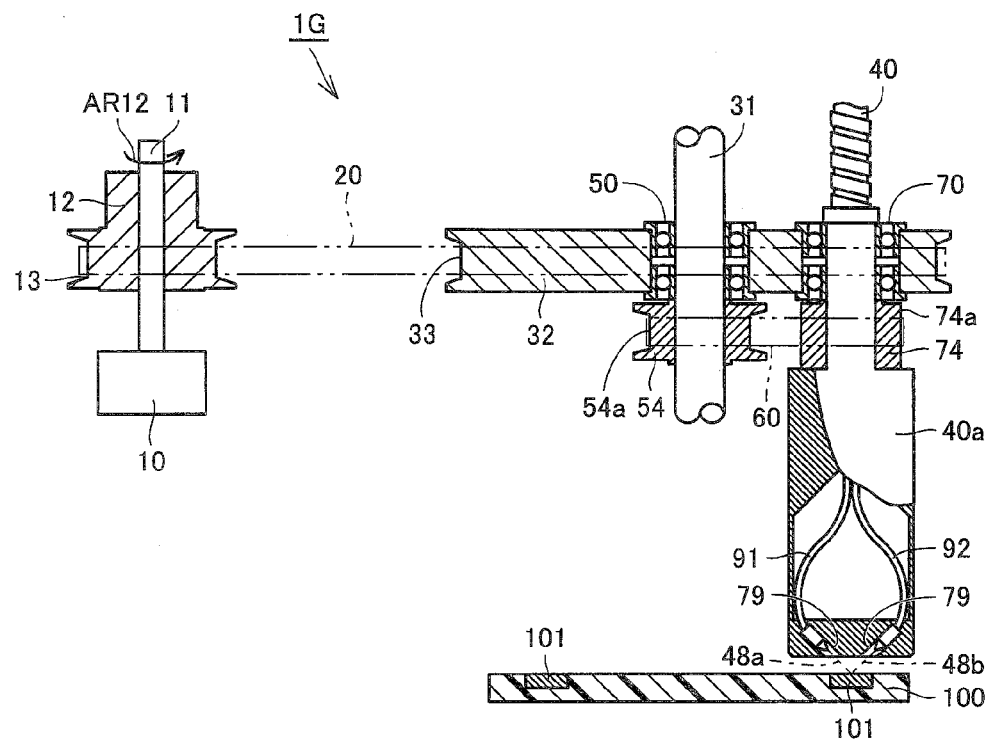
FIG. 22 is a cross sectional view illustrating an optical measurement apparatus in still another configuration of the third embodiment.

Referring to FIG. 22, an optical measurement apparatus 1G in still another configuration of the third embodiment will be described. Here, description will be given on the difference from optical measurement apparatus 1A in the above-described first embodiment.

In optical measurement apparatus 1G, optical fiber 40 has a lower end part 40a configured to be hollow and to have a large diameter, and light projecting fiber 91 and light receiving fiber 92 are disposed inside lower end part 40a. Light projecting fiber 91 and light receiving fiber 92 are exposed in respective openings 79 provided at lower end part 40a. Light projecting fiber 91 and light receiving fiber 92 extend to the vicinity of object to be measured 101.

Detection light 48a projected from light projecting fiber 91 of optical fiber 40 passes through inside lower end part 40a and projected on object to be measured 101 from the vicinity of object to be measured 101. Reflected light 48b from object to be measured 101 passes through lower end part 40a again and directed by light receiving fiber 92 to detector 16 (see FIG. 1).

As with optical measurement apparatus 1G, even with a configuration in which optical fiber 40 is extended to the vicinity of object to be measured 101, no twists occurs in optical fiber 40. Optical measurement apparatus 1G enables measuring the characteristic of an object to be measured (photometric data) with higher accuracy even in a case where light projecting fiber 91 and light receiving fiber 92 are arranged in proximity to object to be measured 101.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An optical measurement apparatus using an optical fiber to measure a characteristic of an object to be measured arranged along the circumference of a circle, comprising:
   a fixed body;
   a rotating body turnable on its own axis at a second angular velocity while revolving about said fixed body at a first angular velocity; and
   said optical fiber held by said rotating body and projecting detection light on said object to be measured and receiving reflected light from said object to be measured,
   said first angular velocity and said second angular velocity are the same in magnitude and opposite in direction.

2. The optical measurement apparatus according to claim 1, wherein
   said fixed body has a first circular portion having a circular external shape,
   said rotating body has a second circular portion having a circular external shape, and
   said first circular portion and said second circular portion have the same diameter, and
   the optical measurement apparatus further comprises an annular belt member surrounding an outer circumferential surface of said first circular portion and an outer circumferential surface of said second circular portion.

3. The optical measurement apparatus according to claim 1, wherein
   said fixed body has a first toothed wheel portion formed like a toothed wheel, and
   said rotating body has a second toothed wheel portion formed like a toothed wheel and having the same diameter as a diameter of said first toothed wheel portion, and
   the optical measurement apparatus further comprises a toothed wheel arranged between said first toothed wheel portion and said second toothed wheel portion.

4. The optical measurement apparatus according to claim 1, wherein
   a revolution direction of said rotating body is reversed every time said rotating body revolves about said fixed body by a predetermined angle.

* * * * *